US00PP26980P2

(12) United States Plant Patent
Nishikawa

(10) Patent No.: US PP26,980 P2
(45) Date of Patent: Jul. 26, 2016

(54) ***CALENDULA* PLANT NAMED '20123-57D'**

(50) Latin Name: *Calendula officinalis*
Varietal Denomination: 20123-57D

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 109 days.

(21) Appl. No.: 14/121,629

(22) Filed: Sep. 29, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguire

(57) ABSTRACT

A new cultivar of *Calendula* plant, '20123-57D', that is characterized by its compact plant habit with strong stems and thick leaves, its double inflorescences with double ray florets that are light yellow in color on the upper surface and yellow (greyed-purple when mature) and suffused with greyed red on the lower surface, its disk florets that are greyed-purple in color and present on about 50% of the inflorescences its long flowering time; blooming for 9 months from spring into winter in Noordwijkerhout, The Netherlands, its very high tolerance to powdery mildew, its very high tolerance to heat and cold, withstanding temperatures below −20° C. in the winter, and its ability to be readily propagated by stem cuttings.

2 Drawing Sheets

Botanical classification: *Calendula officinalis.*
Variety denomination: '20123-57D'.

CROSS REFERENCE TO RELATED APPLICATIONS

This application is co-pending with U.S. Plant Patent Applications filed for plants derived from the same breeding program that are entitled *Calendula* Plant Named '20123-30D' (U.S. Plant patent application Ser. No. 14/120,524)* and *Calendula* Plant Named '20123-5D' (U.S. Plant patent application Ser. No. 14/120,525)*.

BACKGROUND OF THE INVENTION

The present invention relates to a new and distinct cultivar of *Calendula* plant, botanically known as *Calendula officinalis* '20123-57D' and will be referred to hereinafter by its cultivar name, '20123-57D'. The new cultivar of *Calendula* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of vegetatively propagated *Calendula* plants with low-growing and well-spreading growth habits combined with long flowering periods and a unique range of flower colors.

'20123-57D' was selected in the Inventor's trial garden in 2012 as a single unique plant from amongst the seedlings derived from self-crossing an unnamed plant from the Inventor's breeding program, ref. code 20122-18D, in 2012.

Asexual propagation of the new cultivar was first accomplished by stem cuttings in summer of 2012 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish '20123-57D' as a unique cultivar of *Calendula.*

1. '20123-57D' exhibits a compact plant habit with strong stems and thick leaves.
2. '20123-57D' exhibits inflorescences with double ray florets that are light yellow in color on the upper surface and yellow (greyed-purple when mature) and suffused with greyed red on the lower surface.
3. '20123-57D' exhibits disk florets that are present on about 50% of the inflorescences and greyed-purple in color.
4. '20123-57D' exhibits a long flowering time; blooming for 9 months from spring into winter in Noordwijkerhout, The Netherlands.
5. '20123-57D' exhibits very high tolerance to powdery mildew caused by *Podosphaera xanthii.*
6. '20123-57D' exhibits very high tolerance to heat and cold, withstanding temperatures below −20° C. in the winter.
7. '20123-57D' is readily propagated by stem cuttings; *Calendula officinalis* is typically seed propagated.

'20123-57D' can be best compared to plants of the *Calendula* seed strain 'Alice'. 'Alice' differs from '20123-57D' in having flowers that are larger in size, in having a shorter four month long blooming period, in being poorly branched, in being susceptible to powdery mildew, heat, and cold, and in being propagated by seed. '20123-57D' can also be compared to the co-pending *Calendula* cultivars '20123-5D' and '20124-30D'. '20123-5D' differs from '20123-57D' in having inflorescences with ray florets that are a blend of light yellow and peach in color and in lacking any disk florets. '20124-30D' differs from '20123-57D' in having inflorescences with ray florets that are bright yellow-orange in color and in having disk florets on all inflorescences. There are no cultivars of *Calendula officinalis* that are vegetatively propagated known to the Inventor. The Inventor has no records on the characteristics of the parent plant.

BRIEF DESCRIPTION OF THE DRAWINGS

The accompanying colored photographs illustrate the overall appearance and distinct characteristics of the new *Calendula*. The plant in the photograph in FIG. 1 is one year in age as grown outdoors in a 2-gallon container in Katsuta-Gun, Okayama-Pref., Japan. The plant in the photographs in FIG. 1 and FIG. 2 were 5-months in age as grown outdoors in a 13-cm container in Noordwijkerhout, The Netherlands.

The photograph in FIG. 1 provides a side view of the plant habit of '20123-57D' in bloom.

Figure 1:
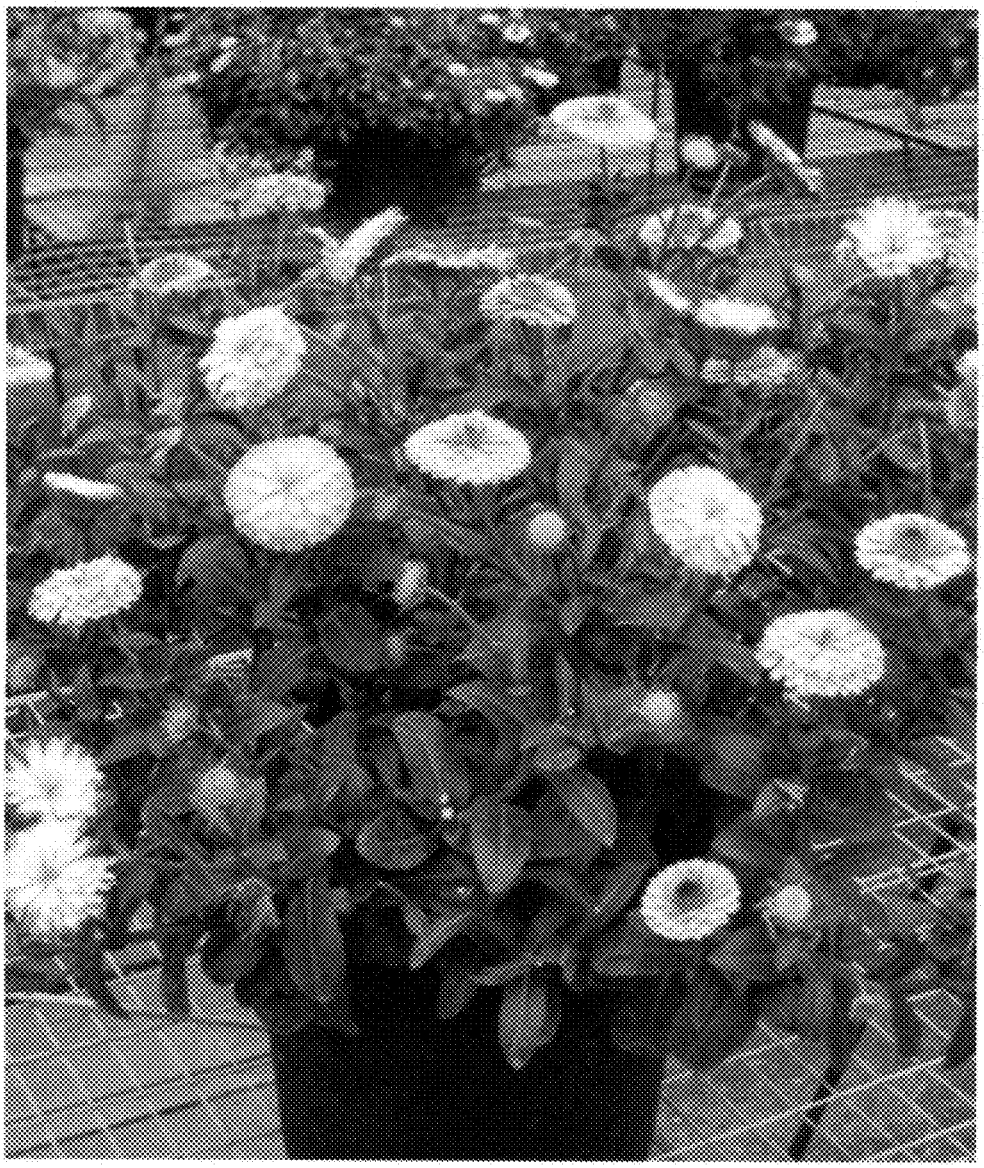
Figure 2:
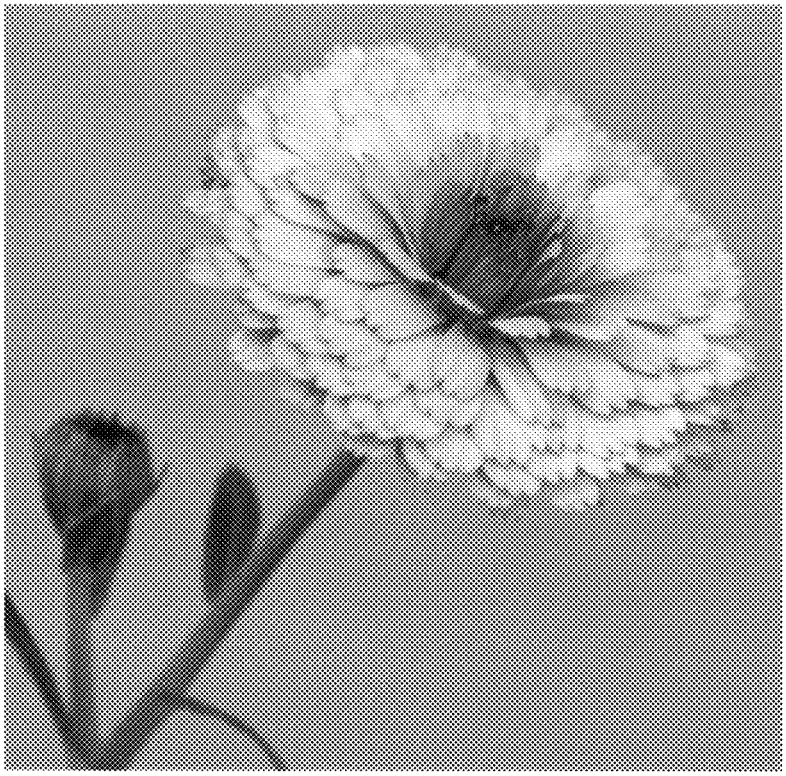
Figure 3:
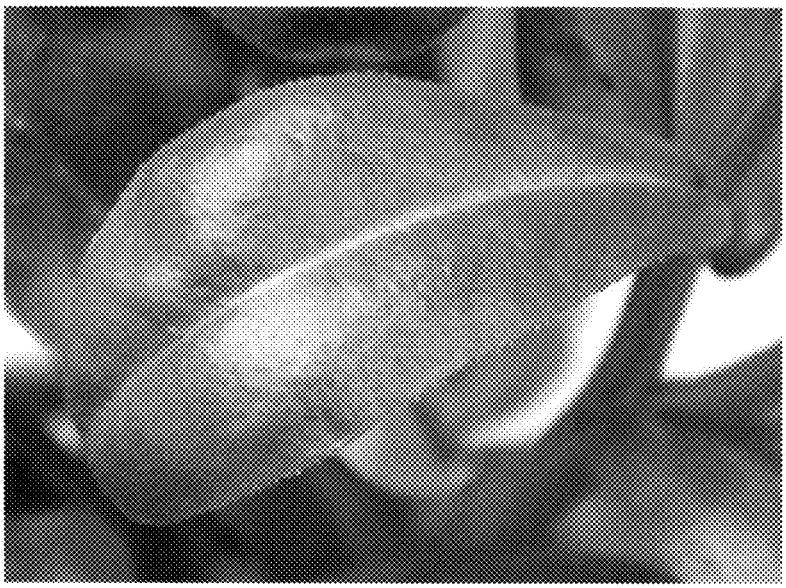

The photograph in FIG. 2 provides a close-up view of an inflorescence of '20123-57D'. The photograph in FIG. 3 provides a close-up view of a leaf of '20123-57D'.

The colors in the photographs may differ slightly from the color values cited in the detailed botanical description, which accurately describe the colors of the new *Calendula*.

DETAILED BOTANICAL DESCRIPTION

The following is a detailed description of five month-old plants of the new cultivar as grown outdoors in 13-cm containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

- *Blooming period*.—An average of nine-months from spring into winter in Noordwijkerhout, The Netherlands.
- *Plant type*.—Herbaceous Perennial and grown as an annual in some climates.
- *Plant habit*.—Compact with strong stems and thick leaves.
- *Height and spread*.—Reaches about 23 cm in height and 23.9 cm in diameter.
- *Cold hardiness*.—Observed to be hardy to U.S.D.A. Zone 7.
- *Diseases*.—Has been shown to have a very high tolerance to powdery mildew caused by *Podosphaera xanthii*.
- *Root description*.—Fine and fibrous roots.
- *Propagation*.—Stem cuttings.
- *Vigor*.—Vigorous.
- *Growth rate*.—About 10 cm a month in spring.

Stem description:

- *Shape*.—Rounded.
- *Stem color*.—144A.
- *Stem size*.—An average of 16.2 cm in length and 4 mm in diameter.
- *Stem strength*.—Strong.
- *Stem aspect*.—Stems grow in an average angle of 35° to the main stem.
- *Stem surface*.—Moderately glossy, sparsely covered with very short soft hairs; 0.3 mm in length and to small to measure color.
- *Stem number*.—4 lateral branches.
- *Internode length*.—Average of 1.8 cm in length.
- *Branching*.—Branches grow from base.

Foliage description:

- *Leaf shape*.—Narrow oblanceolate to spathulate, moderately convexed.
- *Leaf division*.—Simple.
- *Leaf base*.—Truncate to cuneate, decurrent.
- *Leaf apex*.—Obtuse.
- *Leaf venation*.—Pinnate, color: upper surface; 146C, lower surface; 144A.
- *Leaf margins*.—Entire to very sparsely dentate, moderately covered with very short strigose hairs; average length of 0.4 mm and NN155D in color.
- *Leaf attachment*.—Sessile.
- *Leaf arrangement*.—Alternate.
- *Leaf size*.—Average of 7.8 cm in length and 3.2 cm in width.
- *Leaf color*.—Young upper surface; N137B, young lower surface; 137B, mature upper surface; N137A, mature lower surface; between 146B and 147B.
- *Leaf surface*.—Upper and lower surfaces are moderately glossy and moderately rough to the touch, both sides are moderately covered with very short strigose hairs; 0.4 mm in length and NN155D in color.
- *Petioles*.—No petioles present, leaves are decurrent.

Inflorescence description:

- *Inflorescence type*.—Terminal capitulum consisting of ray florets only and a few disc florets.
- *Inflorescence number*.—Average of 1 per lateral stem.
- *Inflorescence fragrance*.—None.
- *Inflorescence aspect*.—Straight on top of stem.
- *Inflorescence longevity*.—A few weeks.
- *Inflorescence size*.—Average of 1.4 cm in height and 4.6 cm in diameter.
- *Inflorescence buds*.—Average of 2 per lateral stem, flattened globular in shape, average of 7 mm in length and 1.2 cm in diameter, color; 138A, top is 166B.
- *Receptacle*.—Flattened globular in shape, 0.2 cm in height and 0.5 cm in diameter, 157D in color.
- *Peduncle*.—3.7 cm in length and 0.2 cm in diameter, terminal peduncle is straight on top of stem, moderate strength, moderately covered with short soft hairs; average of 0.3 mm in diameter and too small to measure color, color of peduncle 143B to 143C.
- *Involucral bracts* (*phyllaries*).—Average of 30 per inflorescence, arranged in 2 rows, lanceolate in shape, narrowly acute apex, cuneate base, margin entire, 6 mm in length, 2 mm in width, surface is glabrous and densely covered with very short pubescence; average of 0.5 mm in length and NN155A in color, color of upper surface 138B with tip 200C, color of lower surface 137A with tip 200C, base 143C.

Ray florets (pistillate):

- *Number*.—Average of 180.
- *Arrangement*.—Rotate, 6 whorls.
- *Shape*.—Oblanceolate.
- *Aspect*.—Slightly upright at the base, held in an average angle of 30° whole ray floret average angle of 10° downward (0°=horizontal).
- *Size*.—Average of 1.6 cm in length and 4 mm in width.
- *Ray floret apex*.—Strongly praemorse to three-tipped.
- *Ray floret base*.—Narrow cuneate.
- *Ray floret margins*.—Entire.

*Ray floret surface*.—Both surfaces glabrous, slightly glossy and velvety.

*Ray floret color*.—When opening upper surface; 4A, when opening lower surface; 11A and suffused with 181A to 181B, when fully open upper surface; 4C, when fully open lower surface; 165B and suffused with 180B to 180C, base 2B.

Disk florets (perfect): An average of 50% of the inflorescences have no disc florets present, in 50% of the flowers with disc florets; an average of 2 disc florets, glabrous and glossy surfaces, placed in the center of the inflorescence with an average of 2 disc florets per inflorescence, shape is tubular, upper $1/6^{th}$ of disk florets free, tip is acute, fused into tube, entire margin, average of 7 mm in length and 2.5 mm in width, color of upper and lower surfaces when opening and fully opened is 183B, mid-section 177D, base is 145D.

Reproductive Organs:

*Gynoecium*.—1 pistil per ray and disk floret, 4 mm in length, stigma unequal decurrent and 183A in color, style is 2 mm in length and 4B in color, ovary 150D in color.

*Androecium*.—5 stamens, filament length is 2 mm and 154D in color, anther shape is linear, 3 mm in length and 11A, tip 200A in color, no pollen.

*Fruit and seed*.—No fruits or seeds have been observed to date.

It is claimed:

1. A new and distinct variety of *Calendula* plant named '20123-57D' as described and illustrated herein.

* * * * *